(12) United States Patent
Lumma

(10) Patent No.: US 7,165,885 B2
(45) Date of Patent: Jan. 23, 2007

(54) X-RAY SYSTEM

(75) Inventor: Waldemar Lumma, Hamburg (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 10/536,921

(22) PCT Filed: Dec. 4, 2003

(86) PCT No.: PCT/IB03/05627

§ 371 (c)(1),
(2), (4) Date: Dec. 27, 2005

(87) PCT Pub. No.: WO2004/052207

PCT Pub. Date: Jun. 24, 2004

(65) Prior Publication Data

US 2006/0126795 A1   Jun. 15, 2006

(30) Foreign Application Priority Data

Dec. 6, 2002  (EP)  .................................. 02102694

(51) Int. Cl.
*H05G 1/02* (2006.01)
(52) U.S. Cl. ...................... 378/193; 378/167; 378/195; 378/197; 378/208
(58) Field of Classification Search ................ 378/167, 378/189, 193, 195, 196, 197, 208, 209
See application file for complete search history.

(56) References Cited

U.S. PATENT DOCUMENTS 5,048,070 A * 9/1991 Maehama et al. .......... 378/197
6,470,519 B1 * 10/2002 Pattee et al. .................... 5/600
6,865,253 B1 * 3/2005 Blumhofer et al. ........... 378/65

FOREIGN PATENT DOCUMENTS

EP    0 373 596 A1    6/1990
EP    0 373 596 B1    6/1990

\* cited by examiner

*Primary Examiner*—Edward J. Glick
*Assistant Examiner*—Chih-Cheng Glen Kao

(57) ABSTRACT

There is described an X-ray system having at least one component (12, 2, 31, 32) that is shiftable (moveable) or pivotable along at least one traverse path to at least one predeterminable locking position (Bx). Components of this kind are in particular the moving parts of a stand such as the moving parts of a ceiling stand (1), floor stand or wall stand for an X-ray generator (2, 21), and the X-ray generator (2, 21) that is fastened to the stand in such a way as to be capable of being pivoted and extended or retracted. Such components also include the shiftable (moveable) or pivotable top of a patient table and a film cassette that is displaceably or pivotably mounted in the table or on a wall stand. The X-ray system is notable in particular for a control unit (122) for sensing a speed of the component (12, 2, 31, 32) when displaced or pivoted along the traverse path and for activating a braking means (124) if the speed is below a predeterminable limiting value and the component (12, 2, 31, 32) has reached the locking position (Bx) or shortly before this.

11 Claims, 2 Drawing Sheets

X-RAY SYSTEM

The invention relates to an X-ray system having at least one component that is shiftable (moveable) or pivotable along at least one traverse path to at least one predeterminable locking position. Components of this kind are in particular the moving parts of an X-ray stand such as a ceiling stand, floor stand or wall stand for an X-ray tube or X-ray generator, or the X-ray tube or X-ray generator that is fastened to the X-ray stand in such a way as to be capable of being pivoted and extended or retracted. Such components also include the shiftable (moveable) or pivotable top of a patient table and a film cassette that is displaceably or pivotably mounted in the table or table top or on a wall stand.

Said X-ray stands are generally used in this case to hold the X-ray generator or X-ray tube over the patient table or, in the case of a wall stand, in front of an area for a patient to be positioned in, behind which the film cassette is situated. To allow an X-ray examination to be performed, and in particular before an X-ray film is exposed, the X-ray tube is displaced and/or pivoted by means of the stand until it has reached the position that is suitable and desired for the exposure.

To locate the X-ray tube by arresting the stand in a specific exposure or triggering position, a plurality of mechanical locking means are usually arranged along the traverse path. These locking means are so designed that, as the X-ray tube is being displaced, they only perform an arresting operation if the speed is below a given limiting value. If the X-ray tube is displaced at a higher speed, it is simply a question of the mechanical latching noises being heard with greater or lesser loudness, without the stand locking into place.

The disadvantages and faults that mechanical locking of this kind involves are principally the fact that considerable vibration may be generated throughout the entire X-ray system by the locking into place. Also, due to the high mechanical stresses, the locking plates may, in time, shift. This in turn produces an undesirable change in the locking positions and thus in the positions in which the exposures are made (the triggering positions). Other disadvantages are that locking of this type is subject to considerable mechanical wear and that is it relatively costly and complicated to adjust the locking positions on site. Finally, even the noises caused by the locking into place are often excessively loud or distracting.

Known from EP 0 373 596 is a carrier device for an X-ray tube that comprises a guide unit mounted on the ceiling of a room for the X-ray tube fastened to a carrier. With it, the X-ray tube can be displaced in a plane parallel to the ceiling of the room and in the vertical direction, to bring it to a central position opposite an X-ray table. Provided along the three traverse paths are a plurality of detectors and a plurality of arresting means by means of which, respectively, the position of the X-ray tube can be detected and the X-ray tube can be arrested in a position. Also provided is an analyzer unit in which is stored positional data relating to the central position of the X-ray table and to a set distance between a focus of the X-ray tube and a photographic exposure system. The unit is also used to compare this positional data with a position sensed by the detectors and to generate an arresting signal when the positional data concerned agrees with the position sensed, and the X-ray tube is thus arrested for an exposure to be made.

However, a particular disadvantage of this device lies in the fact that, if the X-ray tube is moved too fast and is arrested when the correct position is reached, considerable mechanical vibrations may be caused in the whole of the device. Also, considerable cost and complication has to be accepted due to the fact that detectors and arresting means have to be mounted along the entire lengths of the traverse paths in all three directions. Finally, and not least, the user also has to get used to operation that has an entirely different feel because the latching noises that occur with the mechanically locking stands mentioned above do not occur nor is it possible to cause locking into place to occur as a function of the speed of displacement.

It is therefore an object of the invention to provide an X-ray system of the kind detailed in the opening paragraph in which it is possible, at considerably lower cost and complication, for a component that is to be displaced or pivoted to be arrested in a desired locking position in the sense elucidated above at least largely without any trouble.

The invention is also intended to provide an X-ray system of the kind detailed in the opening paragraph in which the risk of local changes, as a result of wear, in predetermined locking positions for a component that is to be displaced or pivoted is ruled out.

What in particular the invention is intended to provide is an X-ray stand of the kind detailed in the opening paragraph in which, when used, the disadvantages and faults explained above that mechanical locking involves, namely particularly the mechanical vibration of the entire system, distracting noises, and increased wear and the change in the locking positions that it involves, do not occur or are at least substantially reduced.

Finally, the invention is also intended to provide a patient table, particularly for use with an X-ray unit, that has at least one component to be displaced or pivoted, such as for example an appropriate table top or a film cassette, and with which, when used, the disadvantages and faults explained above that mechanical locking involves, namely particularly the mechanical vibration of the entire system, distracting noises, and increased wear and the change in the locking positions that it involves, do not occur or are at least substantially reduced.

The object is achieved for an X-ray system in general for an X-ray stand and for a patient table, each of which has at least one component that is shiftable (moveable) or pivotable along at least one traverse path to at least one predeterminable locking position, and a control unit for sensing a speed of the component when displaced or pivoted along the traverse path and for activating a braking means if the speed is below a predeterminable limiting value and the component has reached the locking position or shortly before this.

The particular advantage that this solution has is that the feel in operation that is known from mechanically locking stands is maintained. However, due to the fact that no mechanical locking means or locking plates are required, the vibration of the entire system and the wear that these involve no longer occur or do so to only a considerably smaller degree. The stop distance or stop time of the component could be increased by activating the breaking means already before the component has reached the locking position in order to stop it softly or smoothly.

Claims relate to advantageous embodiments of the invention.

One embodiment can be used to sense both the position of the at least one locking position and the speed of the component.

One embodiment deals with a position-sensing unit that is inexpensive to produce and reliable and accurate in operation.

One embodiment can be used to realize a comfortable and easy to implement slow down of the component if the braking means should be activated before the component has reached the locking position.

Additional embodiments enable the ease of operation to be considerably increased.

One embodiment makes it possible for the component to be arrested in a locking position largely without vibration.

Additional embodiments make it possible, in a relatively easy way, for the locking positions and other operating parameters to be set or selected by a user.

These and other aspects of the invention are apparent from and will be elucidated with reference to the embodiments described hereinafter.

Figure 1:
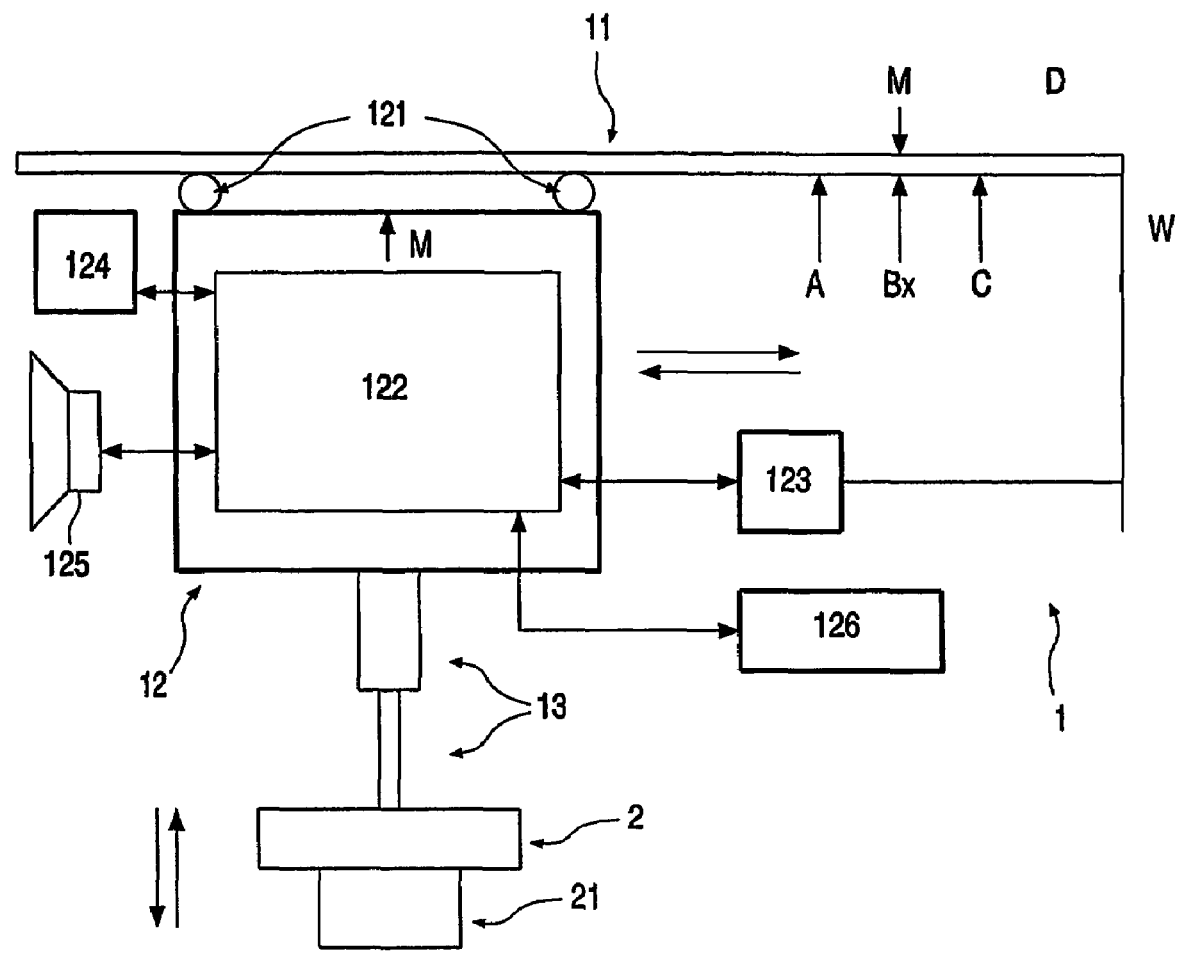
FIG. 1 is a diagrammatic side-view of the principal components of an X-ray system according to the invention.
Figure 1:
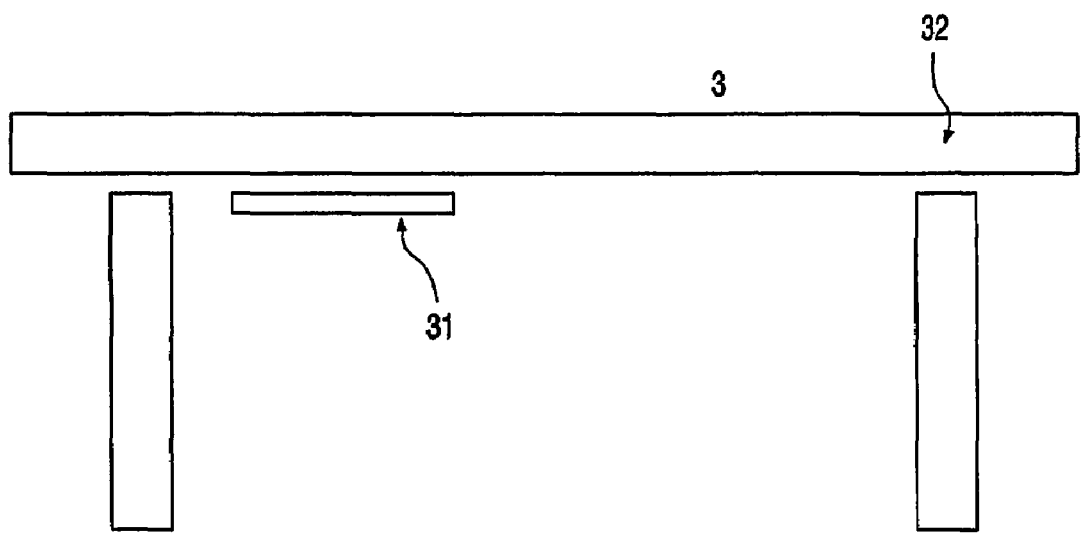

As shown in FIG. 1, an X-ray system according to the invention comprises a ceiling stand 1 by which an X-ray tube 2 or an X-ray generator is held in such a way as to be shiftable (moveable) in relation to a patient table 3 having a film cassette 31 and table top 32.

The ceiling stand 1 comprises a ceiling-stand rail 11 that is fixed to the ceiling D of a room and on which a ceiling-stand carriage 12 is suspended by means of rollers 121. Situated on the ceiling-stand carriage 12 is a telescopic mounting 13 to which the X-ray tube 2 is fastened and by which the latter can be displaced in the vertical direction. There is also generally a collimator 21 mounted on the X-ray tube 2.

The ceiling-stand carriage 12 contains a control unit 122 to which are fed the signals from a position-sensing unit 123, which is used to determine the distance between the ceiling-stand carriage 12 and a wall W of the examination room. Also connected to the control unit 122 is a braking means 124 for the ceiling-stand carriage 12. The braking means 124 is preferably an electromagnetic brake that is active in the de-energized state, that is to say the ceiling-stand carriage is fixed in relation to the ceiling-stand rail 11 and can be released by feeding current to the brake. The braking means 124 may, in general, also be an electrical brake of some other kind and/or a known electromechanical locking means. For example, a magnetic particle clutch or brake can be used.

The braking means 124 and if required the control unit 122 may be so designed that, when the braking means 124 is activated, the ceiling-stand carriage 12 is not halted abruptly but is braked at least sufficiently gently for no unwanted vibrations to occur.

The control unit 122 is also connected to an audio signal transmitter 125. Finally, the control unit 122 may be connected via an interface 126 to a communications bus.

In FIG. 1, there are three positions A, Bx and C indicated by way of example on the ceiling-stand rail 11. The center position Bx is a triggering or locking position for the ceiling-stand carriage 12, while the two positions A and C situated laterally thereof define a window in which the triggering or locking position Bx is situated. As an aid to guide the user of the X-ray system, the location of the triggering position Bx and a reference position on the ceiling-stand carriage 12 may each be identified by a visual marker M.

Once the ceiling stand 1 has been installed, that is to say essentially once the ceiling-stand rail 11 has been fastened to the ceiling D of the room and the ceiling-stand carriage 12 has been hung from the rail 11, and before the X-ray system is used for the first time, one or more triggering positions Bx along the rail 11 at which X-ray exposures are to be made have to be set.

The locations of these triggering positions Bx depend essentially on the type and size of the patient table 3, its set-up relative to the ceiling-stand rail 11, and the location and displaceability in the patient table 3 of a film cassette 31. Virtually as many triggering positions Bx as desired may be set along the rail 11.

These triggering positions Bx are set by first moving the ceiling-stand carriage 12 to a desired position of this kind manually. The location of this position along the rail 11 is then sensed by the position-sensing unit 123 and stored in the control unit 122.

The location is preferably determined by measuring the absolute distance between the ceiling-stand carriage 12 and a fixed point of reference such as the nearest wall W of the room. For this purpose, the position-sensing unit 123 has for example a laser light source or an acoustic source by which, by the transmission of signals to the adjacent wall and the measurement of their transit time, a distance signal is generated and is fed for analysis to the control unit 122. An absolute measurement of this kind has the advantage that the locations of the triggering positions Bx may also be set relatively easily by programming.

As an alternative to this, the location may also be sensed by counting a number of increments during the displacement of the ceiling-stand carriage 12 to the desired triggering position by the optical scanning of an incremental scale along the ceiling-stand rail 11.

Once the location of one or more triggering positions Bx (locking positions) has been determined and stored in the control unit 122 by analysis of the distance signals, a window (A–C) is set about each such position. Basically, the windows may be of different widths, and the triggering positions Bx also need not necessarily be situated exactly in the centers of the windows. The widthwise size of the windows, i.e. the distances of points A and C from the position Bx in FIG. 1, is selected essentially as a function of the mass of the ceiling-stand carriage 12 and of the mass of the items connected thereto, in such a way that operation is pleasant in the manner explained below.

The locations of points A and C are stored in turn, preferably in the form of the absolute distance from a fixed point of reference as explained above, it being possible for this distance to be calculated, from the location of the relevant triggering position Bx and from the width selected for the window, for example by software that is run in a microprocessor unit (once the window width has been entered).

Once a plurality of triggering positions Bx, plus windows A–C respectively associated therewith and their locations, have been determined and stored in the control unit 122, the X-ray system can be put into operation.

The process that takes place in connection with the positioning of the X-ray tube 2, which process is described below, is preferably performed by a software program and by a microprocessor unit that is for example part of the control unit 122.

Once a patient (or an object to be examined) has been placed on the top 32 of a patient table 3, the X-ray tube 2 is displaced manually in the horizontal direction by the operator to one of the triggering positions Bx in which an X-ray exposure is to be made.

As this is done, the positioning-sensing unit 123 transmits the distance signal continuously to the control unit 122. The instantaneous location is determined from this in the control unit 122 and by comparison with a previous, stored location the speed of the ceiling-stand carriage 12 is also calculated.

If the ceiling-stand carriage 12 enters a window enclosing a triggering position Bx (i.e. if it reaches position A from the left or position C from the right in FIG. 1), the instantaneous speed of the ceiling-stand carriage 12 is compared with a limiting value, which was for example entered in the control unit 122 at the same time as the triggering positions and the widths of the windows were set before the X-ray system was put into operation for the first time.

If the speed on entering the window A–C and before reaching the triggering position Bx is below the limiting value or drops below the limiting value, the signal transmitter 125 is driven by the control unit 122 in such a way that it generates a steady signal tone for example. On the triggering position Bx being reached (or shortly before this), the control unit 122 activates the brake 124 so that the ceiling-stand carriage 12 is located (i.e. comes to a gentle halt) at the triggering position. At the same time the signal tone is switched off again.

In order to stop the ceiling-stand carriage 12 softly or smoothly at the triggering position Bx, the stop distance or stop time could be increased by activating the braking means before the ceiling-stand carriage 12 has reached the trigger position Bx. Therefore, if the speed on entering the window A–C and before reaching the triggering position Bx is below the limiting value or drops below the limiting value, the control unit 122 controls (i.e. with a pulse-with modulation) the brake 124 with respect to the available stop distance and the current speed of the of the ceiling-stand carriage 12. As a result, the ceiling-stand carriage 12 can be smoothly, nearly vibration-free and exactly stopped at the triggering position Bx, without any unnecessary efforts for the user.

If on the other hand the speed of the ceiling-stand carriage 12 on entering the window A–C and before reaching the triggering position Bx is above the limiting value or rises above the limiting value, the signal transmitter 125 is driven by the control unit 122 in such a way that it generates an intermittent signal tone for example. The brake 124 is not activated and the ceiling-stand carriage 12 can thus be pushed through the window A–C. On exit from the window, the signal tone is switched off again.

The purpose of the different signal tones being generated is to give the user an audible indication that the ceiling-stand carriage 12 is close to a triggering position Bx and will or will not lock into place in this position. This would also be an easy way of making it possible for the window A–C to be subdivided in respect of the generation of the acoustic signals and for the approach to the triggering position Bx and/or the level of speed to be indicated in an even better way by, for example, an increase in frequency or different frequencies and/or a faster or slower sequence.

In this way it is possible to convey a feel in operation that largely approximates to that of the mechanical locking arrangement explained in the opening paragraphs, which means that, this being the case, there is no need for the user to become accustomed to anything different.

The width of the window may for example be selected in such a way that, by accelerating or slowing down the speed of displacement of the ceiling-stand carriage 12 once it has entered the window, the user can decide whether or not it is to lock into place in the triggering position.

The markings M already explained at the triggering position or positions Bx and at a reference position on the ceiling-stand carriage 12 are used to make the location of the carriage 12 relative to the triggering positions Bx easier to see.

In addition to or instead of the generation of the audio signal, it is of course also possible for a visual signal to be given, for example by a number of LED's laid out in a row that, by being activated, indicate the instantaneous position of the ceiling-stand carriage 12 relative to the triggering position or positions and their windows.

As explained above, the triggering positions are determined and stored before the X-ray system is put into operation for the first time. As an alternative or in addition to this it is also possible, after the X-ray system has gone into operation, for further triggering positions to be stored in the control unit 122 if for example the software is operated in a learning mode. In this case the ceiling-stand carriage 12 is once again moved manually to a desired triggering position and the distance between the position and the wall W is then determined and, together with an appropriate window, is stored, in the manner described above.

The software is also preferably so designed that the width of the windows and the nature of the audio and/or visual signal generated can be set by the user.

Figure 2:
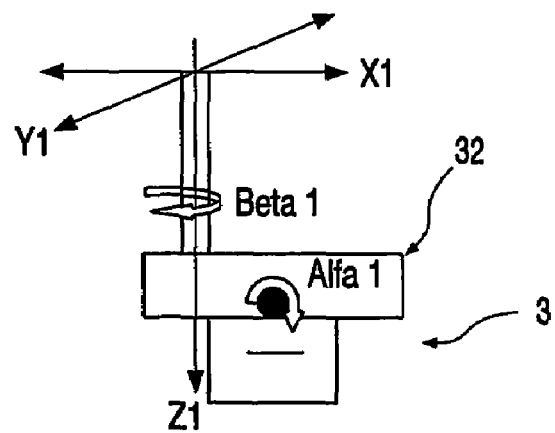
FIG. 2 is a diagrammatic view of a ceiling or floor stand.
Figure 3:
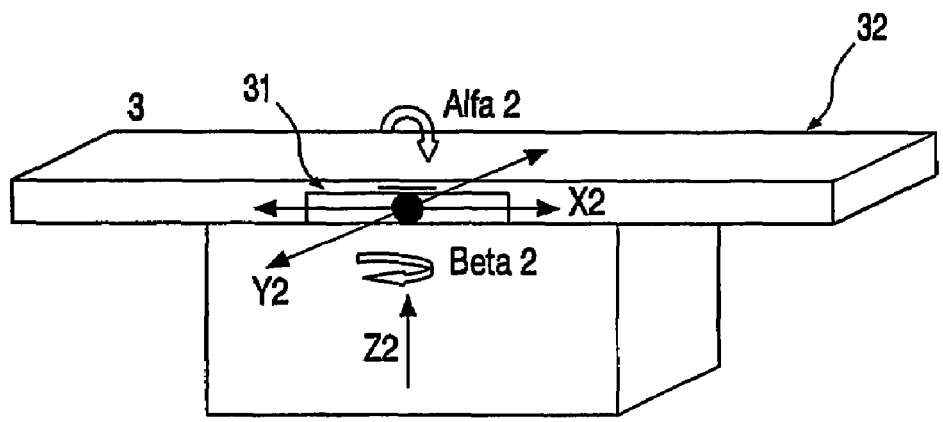
FIG. 3 is a diagrammatic view of a patient table.
Figure 4:
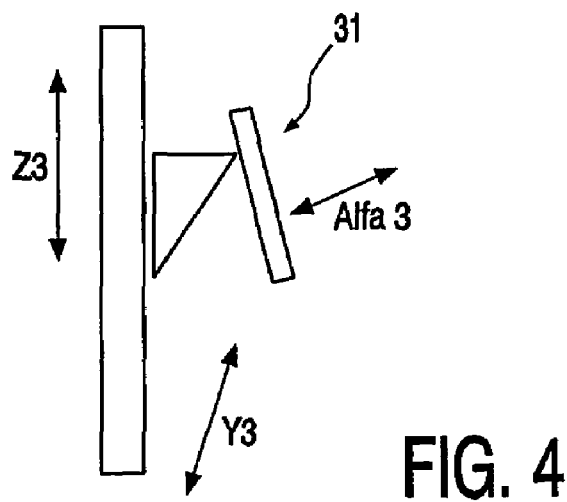
FIG. 4 is a diagrammatic view of a wall stand.

The principle of the invention was elucidated above by reference to the positioning of the ceiling-stand carriage 12 along the ceiling-stand rail 11. It may however also be applied to the positioning of the X-ray tube 2 in the vertical direction and to other linear or pivoting movements such as that of the top 32 of the patient table 3, of the film cassette 31 and of the X-ray tube 2 or generator unit 2, 21. FIGS. 2 to 4 show examples of linear movements of this kind and various pivoting movements that take place in an X-ray system.

FIG. 2 is a diagrammatic view from the side of the directions and axes in, along and about which movements of this kind have to be performed in a ceiling stand and a floor stand. These movements are firstly movements along the X1 and Z1 axes that have already been described above in relation to FIG. 1 (ceiling-stand rail 11 and telescopic mounting 13 respectively). What is often required as well is a movement perpendicular thereto along the Y1 axis. Also, a pivoting movement of the X-ray tube (beta 1) about the Z1 axis and of the top 32 of the patient table 3 (alpha 1) about a horizontal axis may be required where necessary.

FIG. 3 is an enlarged view showing the possible directions of movement and axes at a patient table 3. These are firstly the pivoting movement already mentioned (alpha 2) of the top 32 about the horizontal Y2 axis and a linear movement of the top 32 in the vertical direction along the Z2 axis. Also, the film cassette 31 is generally mounted to be shiftable (moveable) in the plane of the table, i.e. in the Y2 and X2 directions. Finally, what may even need to be considered is a pivoting movement (beta 2) of the top 32 of the table about the vertical Z2 axis.

Finally, FIG. 4 shows a wall stand that for example holds a film cassette 31 for a standing or seated patient.

To allow it to be positioned relative to the patient, the film cassette 31 has to be capable of being moved in the vertical direction along the Z3 axis and, generally, also in a direction perpendicular thereto along the Y3 axis. For certain examinations it may also be necessary for the film cassette 31 to be pivoted out of the vertical through an angle alpha 3.

The X-ray generator (not shown in FIG. 4) may in this case be directed onto the patient with the ceiling stand shown in FIG. 1. For this purpose, the X-ray generator 2, 21 shown in FIG. 1 is so mounted that it can be pivoted to the side through substantially 90°.

The principle according to the invention as described above can be applied to all these movements.

The invention claimed is:

1. An X-ray system comprising:
   at least one component in the X-ray system that is displaceable or pivotable along at least one traverse path to at least one predeterminable locking position;
   a braking means, wherein the braking means comprises an electromagnetic brake that is (i) active in a de-energized state and (ii) released by feeding current to the electromagnetic brake; and
   a control unit configured for sensing an instantaneous speed of the component when displaced or pivoted along the traverse path within at least one predeterminable window of the traverse path, the at least one predeterminable window being defined by two positions of the traverse path situated laterally from and disposed about the at least one predeterminable locking position, the at least one predeterminable window having a widthwise size selected as a function of a mass of the at least one component, the control unit further configured for activating the braking means in response to (i) the speed within the predeterminable window being below a predeterminable limiting value and (ii) the component having reached (a) the locking position or (b) shortly before the locking position.

2. An X-ray system as claimed in claim 1, further comprising:
   a position-sensing unit connected to the control unit, wherein responsive to distance signals transmitted by the position-sensing unit, the control unit is further for determining a location of the component relative to a locking position and for calculating the speed of the component.

3. An X-ray system as claimed in claim 2, wherein the position-sensing unit is provided to measure distance by emitting an acoustic or optical signal and to receive the signal reflected from a point of reference.

4. An X-ray system as claimed in claim 2, wherein the control unit is provided to control the braking means during slow down of the component with respect to (i) the component's speed and (ii) the component's distance to the locking position.

5. An X-ray system as claimed in claim 1, wherein the at least one predeterminable window of the traverse path comprises a widthwise size that is less than the entire traverse path.

6. An X-ray system as claimed in claim 1, further comprising:
   an audio and/or visual signal transmitter, connected to the control unit, for generating a first signal in response to the speed being below the limiting value and a second signal in response to the speed being above the limiting value.

7. An X-ray system as claimed in claim 1, further comprising:
   a visual display for indicating an instantaneous location of the component relative to a locking position.

8. An X-ray system as claimed in claim 1, wherein the control unit comprises a microprocessor unit, and a memory, wherein the control unit stores at least one locking position in the form of a distance from a point of reference in the memory.

9. An X-ray system as claimed in claim 8, wherein the at least one locking position of the component comprises a user selected locking position.

10. An X-ray stand for an X-ray system as claimed in claim 1, wherein the component comprises a part of a stand configured for being displaced and/or pivoted along a traverse path, and/or an X-ray tube or X-ray generator configured for being displaced and/or pivoted along a traverse path.

11. A patient table for an X-ray system as claimed in claim 1, wherein the component comprises a table top configured for being displaced and/or pivoted along a traverse path, and/or a film cassette configured for being displaced and/or pivoted along a traverse path.

* * * * *